United States Patent
Brown et al.

(10) Patent No.: US 6,471,672 B1
(45) Date of Patent: Oct. 29, 2002

(54) SELECTIVE HIGH PRESSURE DILATION BALLOON

(75) Inventors: Brian J. Brown, Hanover; Tracee E. J. Eidenschink, Wayzata; Christopher R. Larson, St. Paul, all of MN (US)

(73) Assignee: SciMed Life Systems, Maple Grove, MN (US)

(*) Notice: Subject to any disclaimer, the term of this patent is extended or adjusted under 35 U.S.C. 154(b) by 0 days.

(21) Appl. No.: 09/437,850

(22) Filed: Nov. 10, 1999

(51) Int. Cl.$^7$ ............................................. A61M 29/00
(52) U.S. Cl. ........................ 604/101.01; 604/101.02; 604/101.05; 604/103.05; 606/194
(58) Field of Search .................... 604/96.01, 101.01, 604/101.02, 101.05, 103.04, 103.05, 104, 107, 523, 532, 536, 912, 915, 919; 606/191–192, 194

(56) References Cited

U.S. PATENT DOCUMENTS

| | | | |
|---|---|---|---|
| 4,328,056 A | | 5/1982 | Snoks |
| 4,338,942 A | | 7/1982 | Fogarty |
| 4,423,725 A | | 1/1984 | Baran et al. ............... 128/207 |
| 4,608,984 A | | 9/1986 | Fogarty |
| 4,744,366 A | | 5/1988 | Jang |
| 5,192,297 A | * | 3/1993 | Hull |
| 5,270,086 A | | 12/1993 | Hamlin .................. 428/35.2 |
| 5,290,306 A | | 3/1994 | Trotta et al. |
| 5,342,305 A | | 8/1994 | Shonk |
| 5,360,401 A | | 11/1994 | Turnland |
| 5,378,237 A | * | 1/1995 | Boussignac et al. |
| 5,447,497 A | | 9/1995 | Sogard et al. |
| 5,453,090 A | | 9/1995 | Martinez et al. |
| 5,462,529 A | * | 10/1995 | Simpson et al. |
| 5,512,051 A | | 4/1996 | Wang et al. |
| 5,536,252 A | | 7/1996 | Imran et al. ............... 604/101 |
| 5,752,934 A | | 5/1998 | Campbell et al. |
| 5,788,708 A | | 8/1998 | Hegde et al. |
| 5,807,398 A | * | 9/1998 | Shaknovich |
| 5,810,871 A | | 9/1998 | Tuckey et al. |
| 5,820,595 A | * | 10/1998 | Parodi |
| 5,826,588 A | | 10/1998 | Forman |
| 5,868,776 A | | 2/1999 | Wright |
| 5,882,334 A | * | 3/1999 | Sepetka et al. |
| 5,919,163 A | * | 7/1999 | Glickman |
| 5,947,977 A | * | 9/1999 | Slepian et al. |
| 5,980,531 A | | 11/1999 | Goodin et al. ............... 606/108 |

FOREIGN PATENT DOCUMENTS

| | | |
|---|---|---|
| WO | 94/19049 | 9/1994 |
| WO | 96/38109 | 12/1996 |

* cited by examiner

Primary Examiner—Michael J. Hayes
Assistant Examiner—Catherine Serke
(74) Attorney, Agent, or Firm—Vidas, Arrett & Steinkraus, P.A.

(57) ABSTRACT

A high pressure dilation medical device delivery catheter having a proximal and distal end comprising two tubes mounted generally concentrically about an inner tube. The balloons being characterized as a relatively short inner tube which is inflated with high pressure and a longer outer tube which is inflated with low pressure. The balloons have independent inflation lumens which extend toward the proximal end of the inner tube. A medical device mounting region is disposed about at least a portion of the outer balloon and may have a stent or other medical device mounted thereupon. A retractable outer sheath is further disposed about the medical device mounting region and is operatively connected near the proximal end of the catheter.

25 Claims, 3 Drawing Sheets

SELECTIVE HIGH PRESSURE DILATION BALLOON

CROSS-REFERENCE TO RELATED APPLICATIONS

Not Applicable

STATEMENT REGARDING FEDERALLY SPONSORED RESEARCH

Not Applicable

BACKGROUND OF THE INVENTION

The present invention relates to medical device delivery systems, particularly dilation balloon catheters employed in applications such as percutaneous transluminal angioplasty (PTA), percutaneous transluminal coronary angioplasty (PTCA) procedures, and more particularly to the utilization of a catheter having multiple inflation balloons for the delivery of medical devices, namely stents.

Balloon catheters, are a highly developed and well known field of medical technology. Balloon catheters are typically used to occlude and seal bodily spaces, expand blood vessels, and deliver a variety of medical devices.

Stents are medical devices that are commonly placed into a body vessel by way of a balloon catheter delivery system. A stent is a prosthesis which is generally tubular and which is expanded radially in a vessel or lumen to maintain its patency. Stents are widely used in body vessels, body canals, ducts or other body lumens.

In many stent delivery applications, the stent is often designed to be self-expanding. When these self-expanding stents are utilized, balloon catheters are typically designed to mount the stent upon the deflated balloon and further surround the stent with a retractable sheath. To actually deliver the stent the sheath is retracted thereby allowing the stent to expand away from the balloon. The balloon is then inflated to seat the stent in place. Stent delivery catheters which utilize a single balloon and a sheath can be seen in U.S. Pat. No. 5,192,297 to Hull, U.S. Pat. No. 5,360,401 to Turnland et al. and U.S. Pat. No. 5,453,090 to Martinez et al.

In the case of a non-self expanding stent, to deploy the stent the catheter must have a means to initially expand the stent from about the catheter and into the target vessel. Typically a balloon is inflated to expand the stent a sufficient diameter about the catheter and then deflated to release the stent. Subsequent to expanding the stent, in many applications the catheter must be completely removed to replace this first balloon with a second balloon more suitable for seating the stent in place, or alternatively an entirely new balloon catheter is used to seat the stent.

In some other applications the laborious and time consuming task of balloon or catheter changeover is avoided by utilizing a catheter which has multiple balloons mounted adjacently to one another. In these applications after an initial balloon expands the stent, the catheter is moved forward in the vessel to put the seating balloon into position under the now expanded stent. While these systems save time by avoiding the extra step of removing the catheter and replacing the balloon, they remain less than ideal as often the balloons are easily ruptured by the edges of the stent and the effect of the entire catheter being moved back and forth in the vessel, in order to properly position the stent, places additional unwanted friction and stress upon the vessel walls.

In many operations which utilize stents, the stent and catheter must often pass through a variety of interferences such as a build up of arterial plaque, hardened calcified legions, or other known medical conditions. The typical low pressure balloon used to expand the stent lacks the required strength, pressure, diameter and compliance characteristics to properly inflate the balloon through these anomalies without risk of rupture or vessel damage. As a result numerous catheter configurations have been developed to address the problems associated with these conditions.

U.S. Pat. No. 5,810,871 to Tuckey et al. discloses a stent delivery system which addresses the stent mounting and balloon puncture problems associated with previous catheters such as those described above, by providing an expandable sheath to be placed between the balloon and stent. Moreover, to protect the vessel from possible tearing as the stent is moved therethrough, the Tuckey catheter employs two end caps which contain the ends of the stent while the stent is compressed prior to expansion. Although Tuckey addresses some of the problems as stated above, Tuckey fails to provide a balloon with compliance, pressure and diameter characteristics for proper seating of the stent as may be required in many applications.

Unlike the catheters discussed above many of the catheters developed for use in PTA procedures utilize complex multiple balloon configurations in order to properly dilate a vessel and clear blockages. U.S. Pat. No. 4,744,366 to Jang is one such PTA catheter.

Although the Jang reference provides a catheter with a dilation region with multiple compliances, it does not provide an easy or atraumatic means to position the balloon in selected regions of the stent.

The Jang catheter uses a plurality of independently controlled balloons having the ability to be inflated over a range of pressures and diameters. As a PTA catheter, the Jang catheter is not designed to mount and deliver a stent. Even if Jang could be modified to deliver a stent, it is unclear from the disclosure if the balloons described by Jang would have the strength and puncture resistance necessary to expand and set a stent.

In order to address the problems described above and to overcome the continued shortcomings suffered by previous balloon catheters, it is an object of the present invention to provide for a medical device delivery catheter capable of inflating and setting the medical device in a vessel without a catheter or balloon exchange, while reducing the possibility of damage to the vessel by the stent or balloons.

A further object is to provide for a multiple balloon catheter capable of expanding a stent with low pressure and seating the stent into place using high pressure.

Yet another object is to provide for multiple balloon catheter capable of expanding a body lumen with low pressure and subsequently seating a medical device into the expanded body lumen using high pressure.

BRIEF SUMMARY OF THE INVENTION

To achieve these and other objects, there is provided a medical device delivery catheter that has multiple inflation balloons. Preferably a catheter having two balloons, an outer balloon and an inner balloon mounted in an essentially concentric manner on the distal end of the inner tube of the catheter. The outer balloon and the inner balloon being used respectively to expand a medical device with low pressure and to then properly seat the medical device in a vessel with high pressure. The inner balloon being capable of motion inside the outer balloon on the catheter shaft. The inventive catheter may have a retractable outer sheath which surrounds the distal end of the catheter prior to delivery of the medical device.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

The following detailed description should be read with reference to the drawings in which similar parts in different figures are numbered the same. The drawings, which are not necessarily to scale, depict exemplary embodiments and are not intended to limit the scope of the invention. Those skilled in the art will recognize that many of the examples provided have suitable alternatives which may also be utilized.

It is well known in the stent delivery art that an entire catheter may be repositioned within a vessel to properly position and seat a stent. However, moving the entire catheter places unwanted strain along the entire length of the vessel. In order to ensure that the inner balloon may be repositioned to properly seat the stent, without requiring that the entire catheter be repositioned, the present invention provides for a stent delivery system having an independently moveable inner balloon for stent seating.

Figure 1:
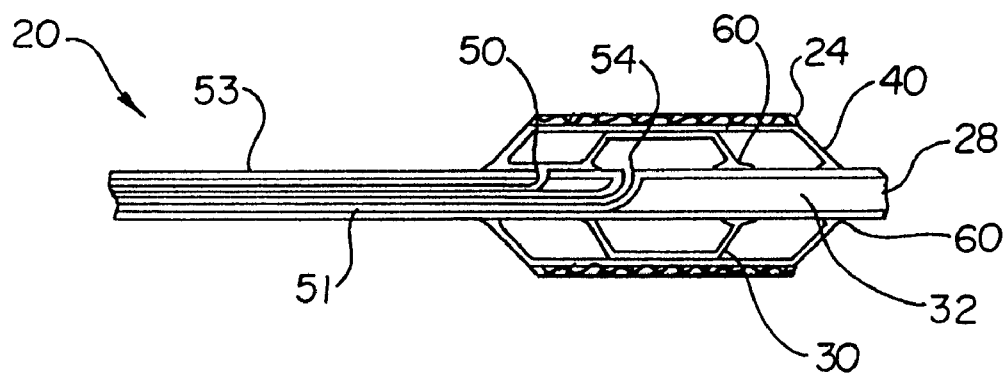
FIG. 1 is an elongated cross sectional view of an embodiment of the medical device delivery catheter showing the balloons in their inflated posture.

The present invention relates to a high pressure medical device deployment catheter. FIG. 1 illustrates a catheter, indicated generally at 20, for deploying a stent 24. As shown, catheter 20 has two balloons, a shorter mobile high pressure inner balloon 30 within a longer low pressure outer balloon 40 distally mounted upon an inner tube or shaft 32. The inner balloon 30 is capable of independent movement relative the inner tube 32. In an alternative embodiment, the outer balloon 40 may be capable of independent motion as well.

In an embodiment where the respective balloons 30 and 40 are individually or both capable of independent movement, the balloons 30 and 40 will respectively include proximal extensions 51 and 53. Where the inner balloon 30 is capable of independent motion the inner balloon 30 may be manipulated as well as inflated from the proximal end of the catheter 20 through proximal extension 51. Likewise, where the outer balloon 40 is independently mobile, the outer balloon 40 may be manipulated and inflated at the proximal end of the catheter 20 through proximal extension 53.

In order for either the inner balloon 30 or outer balloon 40 to be capable of independent motion relative to the inner tube 32, the balloons must respectively be equipped with a sliding seal 60. Slidable seal 60 forms a fluid-tight seal against the inner tube 32 during balloon inflation. The slidable seal 60 will be discussed in greater detail below.

Disposed about inner tube 32, and located proximal of the catheter tip 28 is a medical device mounting region upon which a medical device such as a stent 24 is mounted.

In operation catheter 20 is inserted into a vessel and advanced to a treatment site. Once properly in position, the outer balloon 40 may be inflated under low pressure to initially expand stent 24 and/or dilitate the vessel walls. In an embodiment where outer balloon 40 is not independently mobile, outer balloon 40 may be inflated from within inner tube 32 through low pressure inflation lumen 50. Similarly, in an embodiment where the inner balloon 30 is not independently mobile, the inner balloon may be inflated via internal lumen 54.

Because the low-pressure outer balloon 40 is designed to initially expand stent 24 and to pre dilate a vessel, the balloon will typically be constructed to be highly compliant and readily expandable. The low-pressure balloon 40 is designed to readily expand to a predetermined diameter when inflated with low pressure. An example of some appropriate low pressure volumes may be within the range between 4 and 12 atmospheres, however the required low-pressure values may vary greatly depending on several factors.

In order to ensure proper seating of stent 24 into the vessel, inner balloon 30 is positioned under stent 24 and inflated. Inner balloon 30 may be inflated with a relatively high pressure fluid, from within inner tube 32, through the high pressure inflation lumen 54 or where the inner balloon is mobile through proximal extension 51 as previously discussed. Actual pressure values may vary greatly in actual use, however an example of an appropriate range of values for high pressure inflation may be between 10 and 20 atmospheres.

Figure 2:
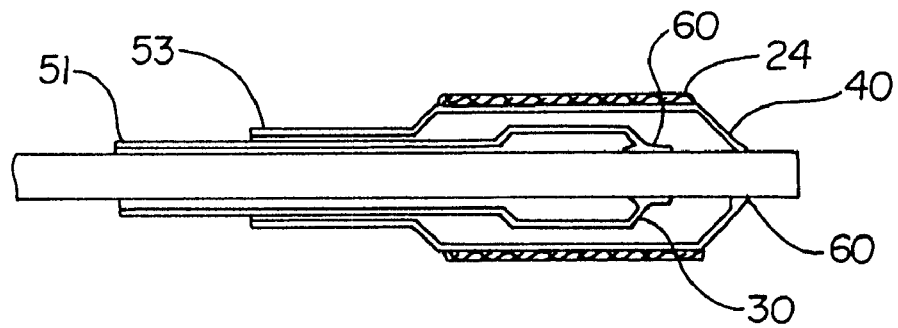
FIG. 2 is an elongated cross sectional view of another embodiment of the medical device delivery catheter.

In a preferred embodiment shown in FIG. 2, both the inner balloon 30 and outer balloon 40 are longitudinally independently mobile relative to the inner tube 32. Inner balloon 30 includes proximal extension 51 which extends all the way to the proximal end of the catheter 20 where the proximal extension 51 and eventually the balloon 30 may be directly inflated and manipulated. By effectively extending the balloon 30 all the way to the proximal end of the catheter, the proximal extension 51 provides a user with the ability to independently position balloon 30 by manipulating the proximal extension 51 while holding the inner tube 32 stationary. Outer balloon 40 is also capable of independent movement and inflation via proximal extension 53.

In contrast to outer balloon 40, inner balloon 30 is preferably designed to continue to expand only marginally when inflated at high pressure. The construction and manufacture of inner balloon 30 provides the inner balloon with sufficient strength to gradually push against and possibly through plaque buildups and other interferences when inflated at high pressure.

Figure 3:
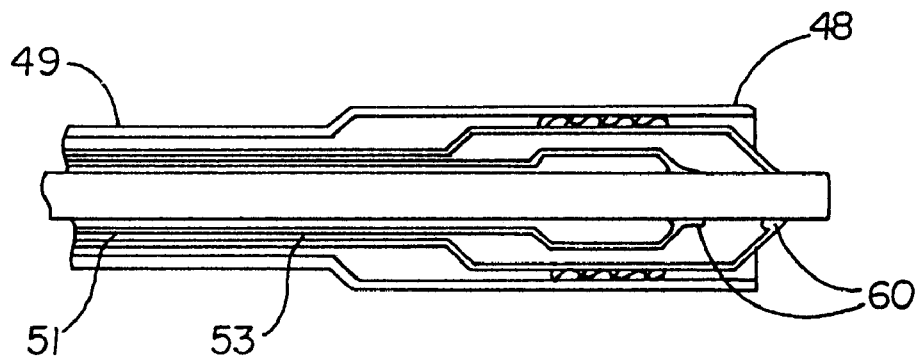
FIG. 3 is an elongated cross sectional view of an embodiment of the medical device delivery catheter including a retractable sheath.
Figure 5:
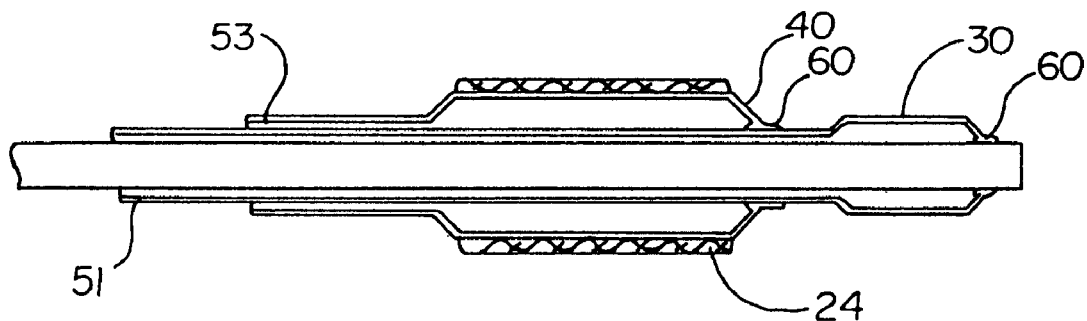
FIG. 5 shows an additional embodiment of the invention wherein the mobile inner balloon is positioned distally relative to the mobile outer balloon.
Figure 6:
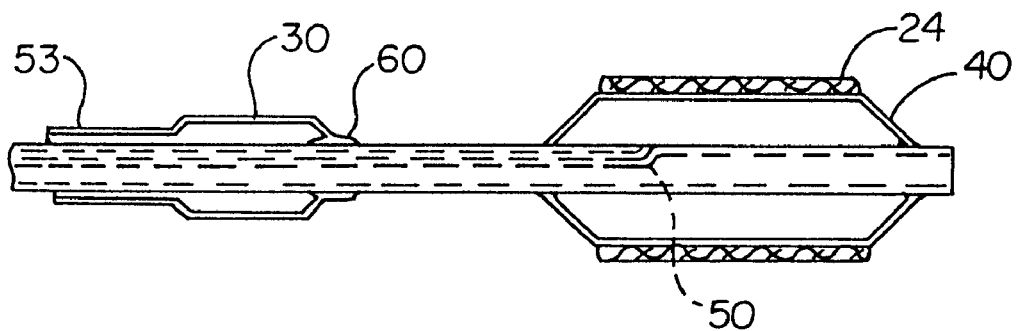
FIG. 6 shows an additional embodiment of the invention wherein the mobile inner balloon is positioned proximally relative to a stationary outer balloon.

In the embodiment shown in FIG. 3 the catheter may be configured with a retractable outer sheath 48, and a retraction member 49. In this embodiment retractable outer sheath 48 surrounds the outer balloon 40 and stent 24. In an embodiment where the inner balloon 30 is located distally or proximally of the outer balloon 40, as best shown by FIGS. 5 and 6, the stent 24 and outer sheath 48 would be disposed about the outer balloon 40.

Figure 4:
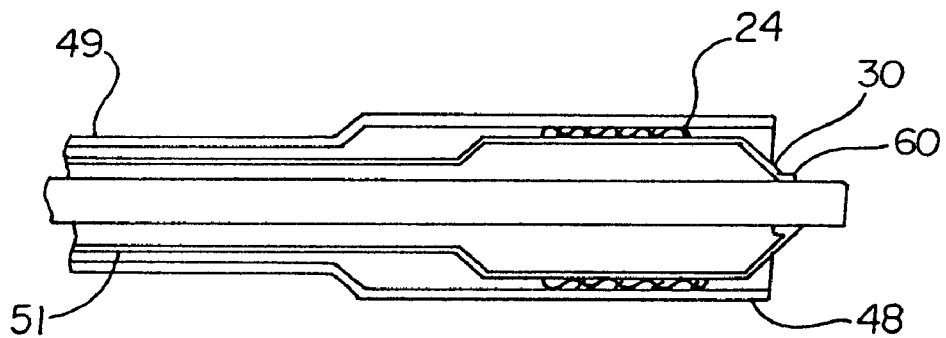
FIG. 4 is elongated cross sectional view of an embodiment of the medical device delivery catheter including only a single mobile balloon and a retractable sheath.

In an alternative embodiment of the invention as shown in FIG. 4, the catheter 20 may avoid the requirement of a low pressure balloon and employ only a single moveable high pressure balloon 30 to seat a self-expanding stent after the stent 24 is freed by the retraction of sheath 48.

Figure 7:
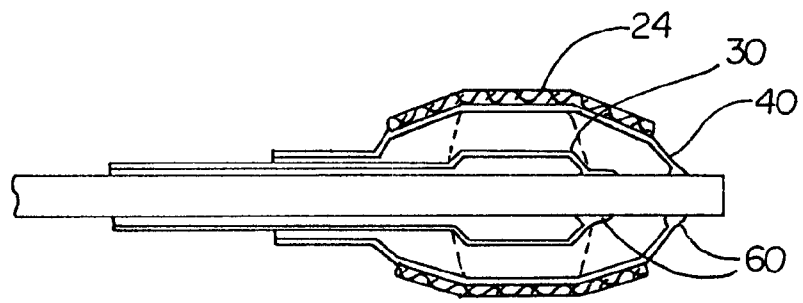
FIG. 7 show an additional embodiment of the invention which illustrates the affect of expanding an inner balloon which has a length less than that of the stent.

As may been seen in FIGS. 1–3 and 5–9, inner balloon 30 will typically be shorter than outer balloon 40. This design feature provides significant benefits when seating the stent in place. Stent 24 will normally be the same or similar in length to the longer outer balloon 40. Inner balloon 30 may be positioned centrally relative to stent 24. As the shorter inner balloon 30 is inflated inner balloon 30 will generally impinge only a central portion of the stent as dictated by the inner balloon's shorter length and position. As shown in FIG. 7, the resulting central expansion of the stent 24 will cause the edges of the stent to have reduced contact with a vessel wall. The extent of the contact is dependant on the design and construction of the stent. By minimizing the contact of the vessel wall and the edges of the stent during the stent seating process, the present high pressure dilation balloon protects the patient from edge dissections which would otherwise be more likely to occur.

Figure 8:
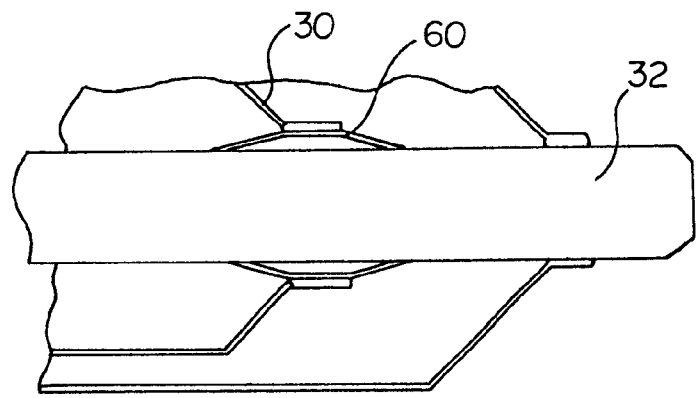
FIG. 8 is close up view of a mobile inner balloon which includes a slidable seal.

As best shown in FIG.8, inner balloon 30 may be slidably sealed to the inner tube 32. The slidable seal 60 allows the inner balloon 30 to be positioned with great accuracy directly under the stent 24. Slidable seal 60 is essentially a fold of inner balloon 30 that rests against inner tube 32. Slidable seal 60 forms a fluid-tight seal as the pressure being exerted upon the seal during inflation of inner balloon 30 forces the slidable seal 60 against the inner tube 32. As shown in FIGS. 2, 3, 5 and 7 outer balloon 40 may also be equipped with a slidable seal 60. As should be obvious from such an embodiment the slidable seal 60 as applied to the outer balloon may be a fold of the outer balloon material which rest against the inner tube 32.

Regardless of the specific embodiment, once the stent 24 is properly set into position both outer balloon 40 and inner balloon 30 are deflated and the entire catheter 20 is withdrawn from the vessel.

As mentioned above, the inventive catheter may contain the stent and balloons in a variety of spatial relationships. In additional embodiments the inner balloon 30 is initially positioned further distally (see FIG. 5) or proximally (see FIG. 6) relative to the stent 24 and outer balloon 40. Where inner balloon 30 is located outside of outer balloon 40, inner balloon 30 remains capable of independent movement along the inner shaft 32. Depending on the specific embodiment desired outer balloon 40 may also be capable of independent movement relative to the inner balloon 30 such as in the embodiment shown in FIG. 5 or the outer balloon may be secured to the inner tube 32 as shown in FIG. 6.

Figure 9:
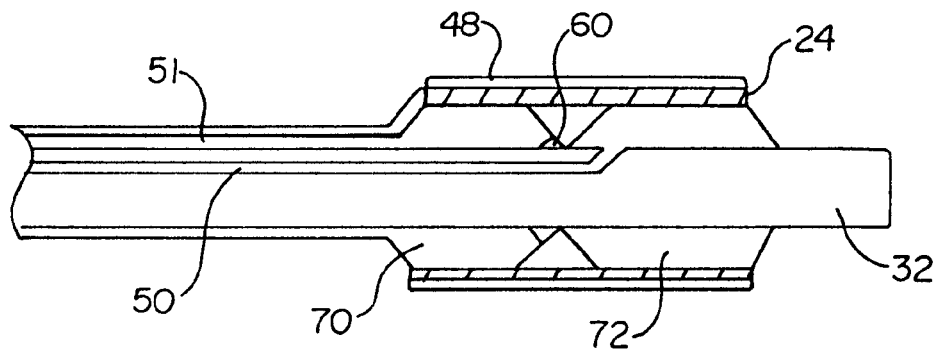
FIG. 9 shows yet another embodiment of the invention wherein two balloons are utilized to inflate different portions of a stent in an adjacent arrangement on the catheter.

In yet another embodiment of the present invention shown in FIG. 9, stent 24 may be disposed about one or more inflation balloons 70 and 72. In the embodiment shown only balloon 70 is capable of independent motion however multiple balloons could be mobile relative to the inner tube 32. The proximal end of balloon 70 is equipped with a sliding seal 60 to allow the proximal extension 51 of balloon 70 to be drawn or advanced as desired without disturbing balloon 72. Balloon 72 may be inflated via lumen 50. Balloons 70 and 72 may be inflated at the same time to provide uniform initial expansion of stent 24. In an embodiment where stent 24 is self expanding retractable sheath 48 may be included to retain the stent on the balloons prior to delivery. Once stent 24 is expanded balloon 70 may be moved to specific areas of the stent and inflated thereby providing the stent with increased pressure for seating the stent or for compressing plaque or other interferences between the stent and vessel wall.

In all of the embodiments described above, the balloon may be composed of suitable materials which include polyolefin copolymer, polyester, polyethylene terephthalate, polyethylene, polyether block amide, polyamide, polyimide, nylon, latex and urethane as well as other suitable balloon materials as are known in the art.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A catheter with an expandable portion comprising:
   (a) a central elongated catheter element extending through the expandable portion, the expandable portion comprising a fixed balloon;
   (b) a moveable balloon carried on the central elongated catheter element, constructed and arranged for axial movement thereon, the movable balloon being slidably sealed to the elongated catheter element, and
   (c) an inflation means operatively associated with the moveable balloon for independent inflation thereof, the inflation means comprising a fist inflation lumen in fluid communication with the fixed balloon and a second Sxflation lumen in fluid communication with the moveable balloon.

2. The catheter of claim 1 further comprising a medical device mounting region disposed about at least a portion of the expandable portion.

3. The catheter of claim 2 further comprising a retractable outer sheath disposed about the medical device mounting region, the retractable outer sheath having a retraction means that extends proximally.

4. The catheter of claim 1 wherein the elongated catheter element defines an inner lumen.

5. The catheter of claim 4 further comprising a guide wire which resides at least partially within the inner lumen.

6. The catheter of claim 5 having a configuration selected from the group consisting of rapid exchange catheters, over-the-wire catheters and fixed wire catheters.

7. The catheter of claim 1 wherein the moveable balloon is contained within the expandable portion and axially moveable therein.

8. The catheter of claim 7 further comprising a medical device mounting region disposed about at least a portion of the expandable portion.

9. The catheter of claim 8 further comprising a retractable outer sheath disposed about the medical device mounting region, the retractable outer sheath having a retraction means that extends proximally.

10. The catheter of claim 9 wherein the inflation means further comprises a first inflation lumen in fluid communication with the expandable portion, and a second inflation lumen in fluid communication with the moveable balloon.

11. The catheter of claim 10 herein the elongated catheter element defines an inner lumen.

12. The catheter of claim 11 further comprising a guide wire which resides at least partially within the inner lumen.

13. The catheter of claim 12 having a configuration selected from the group consisting of rapid exchange catheters, over-the-wire catheters and fixed wire catheters.

14. A catheter having a proximal end and a distal end portion comprising:
(a) a first balloon carried on a distal end portion of the catheter;
(b) a central elongated catheter element extending through the first balloon;
(c) a second balloon carried on the central elongated catheter element, constructed and arranged for axial movement thereon, the movable balloon being slidably sealed to the elongated catheter element; and
(d) an inflation means operatively associated with the first balloon and second balloon, respectively for independent inflation thereof.

15. The catheter of claim 14 wherein the second balloon is constructed and arranged for inflation at a higher pressure than first balloon.

16. The catheter of claim 15 wherein the first balloon is longer than the second balloon.

17. The catheter of claim 16 further comprising a retractable outer sheath disposed about the medical device mounting region, the retractable outer sheath having a retraction means that extends proximally.

18. The catheter of claim 14 wherein the second balloon is located at least partially within the first balloon.

19. The catheter of claim 14 further comprising a medical device mounting region disposed about at least a portion of the first balloon.

20. The catheter of claim 14 wherein the inflation means further comprises a first inflation lumen in fluid communication with the first balloon, and a second inflation lumen in fluid communication with the second balloon.

21. The catheter of claim 14 wherein he elongated catheter element defines an inner lumen.

22. The catheter of claim 21 further comprising a guide wire which resides at least partially within the inner lumen.

23. A catheter having a proximal end and a distal end comprising:
(a) a first balloon carried on a distal end portion of the catheter;
(b) a second balloon located within the first balloon and carried on the central elongated catheter element, the second balloon constructed and arranged for axial movement within the first balloon and being slidably sealed to the elongated catheter element;
(c) a medical device mounting region disposed about at least a portion of the first balloon, and (d) an inflation means having a first inflation lumen in fluid communication with the first balloon, and a second inflation lumen in fluid communication with the second balloon, operatively associated with the first balloon and second balloon, respectively for independent inflation thereof.

24. The catheter of claim 23 further comprising a retractable outer sheath disposed about the medical device mounting region, the retractable outer sheath having a retraction means that extends proximally.

25. A catheter having a proximal end and a distal end portion comprising:
(a) a first balloon carried on a distal end portion of the catheter;
(b) a central elongated catheter element extending through the first balloon;
(c) a second balloon carried on the central elongated catheter element, constructed and arranged for axial movement thereon and being slidably sealed to the elongated catheter element, the second balloon being positioned at least partially within the first balloon; and
(d) an inflation means operatively associated with the first balloon and second balloon, respectively for independent inflation thereof.

* * * * *